United States Patent [19]

Thomas et al.

[11] 4,063,560
[45] Dec. 20, 1977

[54] CRYOSURGICAL INSTRUMENT

[75] Inventors: Ernest Hilton Thomas, Collingbourne Kingston, near Marlborough; Humphry Robert Evatt, Andover, both of England

[73] Assignee: Spembly Limited, England

[21] Appl. No.: 674,032

[22] Filed: Apr. 5, 1976

[30] Foreign Application Priority Data

Apr. 22, 1975 United Kingdom ............... 16595/75

[51] Int. Cl.² ............................................. A61B 17/36
[52] U.S. Cl. .................................................. 128/303.1
[58] Field of Search ....................................... 128/303.1

[56] References Cited

U.S. PATENT DOCUMENTS

| 3,393,679 | 7/1968 | Crump et al. | 128/303.1 |
| 3,502,081 | 3/1970 | Amoils | 128/303.1 |
| 3,512,531 | 5/1970 | Crump et al. | 128/303.1 |
| 3,548,829 | 12/1970 | Reynolds et al. | 128/303.1 |
| 3,613,689 | 10/1971 | Crump et al. | 128/303.1 |
| 3,696,813 | 10/1972 | Wallach | 128/303.1 |
| 3,913,581 | 10/1975 | Ritson et al. | 128/303.1 |

Primary Examiner—Channing L. Pace
Attorney, Agent, or Firm—Shapiro and Shapiro

[57] ABSTRACT

The invention provides for re-warming of a cryosurgical instrument after its use in the cold mode, during which refrigerant is supplied through a first duct through first restriction, by admitting to the cavity within the probe tip fluid from a pressurized source through a second duct this supply being subject to control imposed by a second restriction.

19 Claims, 4 Drawing Figures

CRYOSURGICAL INSTRUMENT

The invention relates to cryosurgical instruments in which a so-called probe or probe tip, or applicator, is cooled by the passage through its hollow interior or cavity of a fluid refrigerant. In particular, the invention is concerned with such instruments which when cooled either by a polyatomic gas expelled by the pressure of its source cools by the Joule-Thomson effect upon expansion (that is to say as the result of isenthalpic expansion); or by evaporation if the refrigerant be stored as a liquid, such cooling being effected within the instrument. In both the Joule-Thomson and the evaporative systems, cooling is the result of the refrigerant fluid suffering a drop of pressure caused by restriction through which the fluid passes. Such restriction and consequently the cooling takes place, in the kind of instrument, within the instrument itself, and therefore the refrigerant reaches the instrument from the source at, or substantially at, the source pressure and temperature and the cooling occurs in the immediate vicinity of the probe tip. In this kind of instrument the refrigerant occupies the cavity of the probe as a cold gaseous fluid cooled either by isenthalpic gaseous expansion only or by evaporation and taking up latent heat of vaporisation which it derives from the wall of the cavity and therefore from the tissue with which the probe or applicator is contacted. The cold gaseous fluid may carry with it some proportion of liquid refrigerant in the form of droplets or mist.

In the foregoing, "cryosurgical" is deemed to include the usages of hypothermal treatment for example therapeutically or cosmetically, by the contacting of a cooled surface (which surface for present purposes is included in the term "probe", or "applicator"), with animal tissue. It is also to be taken that where, herein, reference is made to "tissue", in appropriate context the word is intended to include liquid secretions associated with tissue or other inclusions, as if part of the tissue.

It is usually important that such a cryosurgical instrument be quickly and precisely controlled in the cooling, refrigeration, or "freezing" phase; we believe that it is of comparable importance to control warming, defrosting, (or "thawing") of the instrument, particularly because it is desirable that it can quickly be released from the congelation with the tissue which it effects. Such warming involves a release or supply of heat, such as to raise the temperature of the probe and thereby the tissue and whatever other material constitutes their interface, such as saline solution deliberately used at such interface.

In the art of cryosurgical instruments, there have been proposed ways of warming the probe (to effect the warming mode) after using it as a refrigerated implement (i.e. in the freezing mode). In U.K. Patent No. 1,111,757 U.S. Pat. No. 3,502,081 and a number of Patent Specifications related thereto, Amoils and others disclosed in some detail, electric resistance warming. This has had considerable success in the surgical field. In his South African Patent Application No. 3391/65 (accessible to the public for example as a certified document of record in support of the Application for U.K. Pat. No. 1,111,757 above referred to, in May 1968) Amoils propounded that warming in a cryosurgical instrument should be provided for by blocking the exhaust flow from the probe by closing a valve. This suggested the result that gas from the source being rapidly increased in pressure, should condense in the probe and therefore rewarm the probe by reason of giving up latent heat.

In U.S. Pat. No. 3,696,813 (and in consequential Specifications in other countries) Wallach identified warming by exhaust blocking, to the same effect as that which was previously identified by the previously published Amoils South African Specification.

In his contribution to the art, Wallach proposed a cryosurgical instrument cooled by the Joule-Thomson effect, and warmed by blocking off the exhaust so that there would be a quick rise of pressure within the probe. It was not explicit in the prior art, that whilst interruption by stopping off the exhaust resulted in an increase of pressure within the probe, the important effect was to cause condensation of the gas arriving therein by reason of the pressure increase, and that such condensation must be accompanied by the giving up of latent heat, resulting in warming of the probe. However, at least in some instruments and especially those (such as ophthalmic) where speed is an important factor, the rate of warming of the probe tip resulting from blocking the exhaust, is unsatisfactorily slow, maybe say 10 to 30 seconds for tissue release, whereas a desirable time for a warming mode is measurable in fractions of a second.

It is convenient to refer to these earlier Amoils and Wallach teachings as "exhaust blocking" control; in both cases warming was proposed by blocking the exhaust from a Joule-Thomson type probe by valve means, so that pressure of the supplied gas builds up within the probe until it balances the source pressure, the rate of flow of the gas entering the tip cavity of the probe by its ordinary path (i.e. through the refrigerating restriction) decreasing as the pressure difference between the pressure source and the cavity sink (i.e. the probe cavity and its immediately adjacent passage volumes) diminishes: likewise the rate of flow from the source to the sink, which is subject to the control exercised by the restriction similarly decreases.

Designers of such instruments have to be alert to mechanical risk due to the fact that the whole structure of the probe (and any other elements similarly subjected to internal pressure) is subjected to the full source pressure when the instrument is in the warming mode. Since it is generally desirable to construct the probe tip with a very thin wall and it is in practice a necessity to provide various joints, there is some risk of mechanical failure. High thermal conductivity of the probe tip is desirable, and metals selected for high conductivity are often of low mechanical strength. Thus from the purely mechanical point of view the designer must have regard to the risk involved in the use of high internal pressure. Nevertheless this risk is tolerable in some cases and is, in practice, to some extent mitigated by the simplicity of construction which it involves: indeed in the present invention the probe may be subjected internally to the full source pressure in some examples.

There is, however, also some disadvantage in exhaust blocking control from the fluidic or thermodynamic point of view. For example, in the warming mode, when the exhaust valve is closed refrigerant gas will liquefy on some cooled surface in or connected with the instrument (e.g. tip cavity, exhaust passage, exhaust valve) at which fluid contact occurs; a considerable volume of liquid may thus accumulate. Should there be such an accumulation of liquid at a particular locality, negligible further heat is available for warming in that locality. This effect is likely to be greater in instruments having large mass, than in the smaller sizes an example of which is an ophthalmic probe.

Another disadvantage of previously proposed exhaust blocking control is that in probes operating by the Joule-Thomson effect and in which the flow rate is limited by the refrigerating restriction to a very low rate, the rate of warming (being due to a similarly limited flow rate will be correspondingly reduced.

Also in such probes, leakage e.g. past the exhaust valve if of a similar order to passage through the refrigerating restriction, may result in failure to pressurise the cavity adequately and consequent inadequacy of warming.

The present invention aims to provide a way of warming which not only minimises all or some of the disadvantages of previously proposed ways above mentioned (e.g. of electrical or exhaust valve warming) but has positive advantages, e.g. speed of warming, convenience of use, and simplicity of construction, and a further potential advantage in some examples, namely warming by flow-controlled effects without involving the risks attended upon high pressure within the probe. The invention may be considered as an attractive alternative to, and in some respects an advance from that which is described in U.K. Application No. 25910/72 and U.S. Pat. No. 3,913,581 in which the inventors were Ritson and Thomas. This latter invention involves what is conveniently called "reverse flow" warming (as contrasted with "exhaust blocking" warming) and it involves the provision in a Joule-Thomson type of instrument, of a line of connection in which there is no deliberately-provided restriction between a source of pressure gas and the cavity of a cryosurgical probe, so that the operator can operate valve means so as to admit warming gas at substantially ambient temperature (i.e. temperature which is not significantly below the ambient) and at a high rate, into the cavity where such gas performs the required warming. The gas performs the warming largely or partially by condensing within the probe, the condensate then being allowed to escape as a liquid, or partly as a liquid and partly as a gas, being purged to atmosphere by following or entraining gas, the probe temperature having been raised by the latent heat. Liquid condensate remaining within the probe may be purged by venting or subsequently to warming, maybe during the early part of the next cooling mode. This Ritson and Thomas invention has been found to be highly effective and quick in the warming mode when applied to relatively small instruments, such as those which are adapted for ophthalmic use. In instruments adapted to operate on a larger scale, however, wherein by virtue of higher refrigerant flow through larger volumes, cooling of the exhaust passage (including exhaust valves) is greater, liquid condensate is likely to form preferentially in the exhaust rather than within the cavity, and may subsequently flow into the cavity, this leading to partial failure to warm or unacceptably slow warming. It is a practical advantage to the user, if means be provided to regulate the flow into the probe of warming gas in the warming mode so as to result in proper functioning and simple operator's control in an instrument which may have a wide range of probe sizes and shapes. This matter of "wide range" can be expressed another way, namely "adaptability". By the present invention it is possible to use in the warming mode, substantially permanent restriction means in the control system (which may be a console or hand-held control system) which is able to cover the requirements of a wide range of probe sizes and kinds, so that one such system, unchanged, is available as a piece of capital equipment, at the service of surgeons who may have quite different operations to perform and therefore probes of widely different cooling capacity and rate of flow. It is one of the aims of the invention to provide this advantage.

The invention also provides variants in which as the result of some simple selective action, the so-called "permanent" restriction may be changed so as to cover a further range or ranges of probe size.

In some variants of the invention it may occur that there is reversal (from the normal operative sense) of flow, which may serve to purge material the presence of which may tend to block the desired flow of fluid.

The present invention relates to a cryosurgical instrument of the kind in which there is a probe having a tip or applicator with a wall of thermally conductive material enclosing a cavity into which (in the cooling mode) is led through a first duct a supply of refrigerant fluid from a pressure source into the probe cavity in which probe the refrigerant, of which the rate of flow is controlled by its passing through a first restricton, expands with a pressure-drop either with Joule-Thomson cooling and/or with evaporation resulting in cooling, the resultant gas escaping (in the cooling mode) through an exhaust duct. Escaping gas in such kind of instrument may, as previously, be arranged to cool incoming fluid regeneratively.

In the present invention, as in the Ritson case above referred to, in the warming mode a warming fluid is supplied into the cavity under pressure whilst at substantially ambient temperature or at a temperature high relatively to the probe temperature achieved in the cooling mode.

Reference to regeneration is made above. However, it may be found desirable deliberately to avoid regeneration which in some cases may be detrimental to freezing performance. Therefore, gas streams may be deliberately thermally separated.

According to the present invention there is provided an instrument of the kind stated in which fluid from a pressurised source is fed to the cavity of the probe tip through a first duct in which there is within the instrument such restriction as to produce a pressure-drop from approximately the source pressure to the cavity pressure resulting in the required temperature drop within (and therefore of the wall of) the cavity, which instrument is further provided with connection for the supply into the cavity of pressurised fluid by way of a second duct, the flow through which second duct is subject to restriction such that the flows through said ducts and therefore said first and second restrictions pressurise the cavity in the warming mode so as to result in condensation therein, the first and second restrictions being so characterised as to control the sense of direction of flow of fluid into the cavity.

It is to be understood that the second restriction need not be in the second duct. It may be in a vent from the cavity, and still result in controlling flow through the second duct by reason of controlling build-up of pressure in the cavity. Similarly it (the second restriction) may be in a branch off the second duct which branch allows venting to atmosphere.

An instrument provided as above, may be supplied with a polyatomic gas from a pressured source (e.g. a bottle of stored liquid) the instrument being cooled by the Joule-Thomson effect, in the manner known per se.

In such case the same source may be used to supply the second duct in the warming mode, warming being then attributed to condensation of the gas in the cavity. As will be seen, there may be provision for purging condensate from the cavity or its neighbouring ducting etc.

The invention includes aspects of connections and valves which may be used, and also pressure controlled actuating means whereby the operation of valves is facilitated.

When the invention includes venting from the cavity of the warming gas, an advantageous result is purging from the cavity and associated ducting such liquid as may be present. In some circumstances this may afford the further advantage of enhancing the effectiveness and speed or warming.

The warming effect is, as will be seen, controlled by valve means which may be manually operable or remotely controlled and such means may include or may be interconnected with an exhaust valve means so as to operate simultaneously or closely in sequence therewith.

There are cases, however, in which the valve arrangements may quite satisfactorily simply provide for warming gas flow and exhaust cut-off, in which case the warming gas pressure exerted in the probe and built up therein at a rate subject to the control of pressure exercised by the second restriction is arranged to reach equality with and therefore to balance the pressure of the refrigerant fluid which is exerted in the cavity by the first duct. This immediately suggests that the source of refrigerant fluid and that of the warming gas be at the same pressure, which is quite simple to provide since they may be one and the same source, and (as in the Ritson teaching previously mentioned) this is very simply accomplished by using a two-way valve in the supply line between the gas source and the instrument.

The invention includes a cryosurgical instrument comprising a probe or applicator having a tip adapted by shape and material to be suitable to contact animal tissue and transfer heat therefrom into a fluid refrigerant medium the so-called tip constituting an envelope of high thermal conductivity which encloses a cavity, a first conduit opening into said cavity and such as to conduct refrigerant fluid from a pressure source through a first restriction controlling the rate of flow and resulting in a drop of pressure through it so that the fluid which has entered said cavity experiences a reduction of temperature sufficient usefully to effect said heat transfer (viz. to cool) by reason of the decrease of pressure from the source pressure to the cavity pressure (whether by Joule-Thomson expansion or evaporation), an exhaust conduit leading from said cavity to external ambience, usually the atmosphere, when an exhaust valve in said exhaust conduit so dictates, a second conduit controlledly to supply said cavity with gaseous refrigerant under a pressure from a source which is substantially equal to that of said pressure source, the rate of flow through which second conduit being subject to the control of a second restriction, and means to co-ordinate the flow of fluid from the second conduit into the cavity with the action of the exhaust valve, so that the latter is wholly or partially closed whilst fluid from the second conduit may supply the cavity.

The second restriction may be situated within a control console or equivalent supply equipment, remote from the cryosurgical probe or may be within an instrument designed to be held in the hand.

A two-restriction system as above outlined and according to the invention can readily be designed so that the flow characteristics of the second restriction are suitable without change for use in conjunction with a wide variety of sizes of first restriction. Thus it results that with great simplicity excellent warming is achievable with a wide variety of probes, using only a single unchanged control "console" (as so called). This is highly convenient and economic, the console being a relatively costly piece of equipment. If, however, there were reason to provide an even wider coverage of probes then two or more second restrictions may be provided in duct branches which are in parallel and there may be any form of selector valve means so that a smaller or larger second orifice or orifices in parallel may be brought into use. Such further restrictions may easily be embodied in the console.

Thus the second restriction, whether in a console or embodied in a hand held instrument or be an adjustable valve, may be a selectably set valve; or may be such as to be readily exchangeable. The selection may be subject to the operation of a pipe-coupling, in the manner of a plug and socket coupling, the position of engagement of which may be effective to select the characteristics of the second restriction.

Thus the invention may provide changeover valve means (or provision for interchangeability) such that, and so ducted that, a smaller or larger first restriction, or restrictions in parallel, may be brought into use, for example where detachable tips are to be employed for varied surgical purposes, and it be preferred to use different flow rates, so that improvement in warming rate, economy of refrigerant consumption, and/or minimising of cooling in parts of the instrument remote from the probe tip or applicator may be achieved.

When reference is made to venting to atmosphere, it is to be assumed that the function may involve a length of conduit such as to lead vented fluid remotely from the site of surgery; and the atmosphere may be that which exists in some form of container or other provision for disposal.

The invention will now be described with reference to the accompanying diagrammatic drawings in which.

Figure 3:
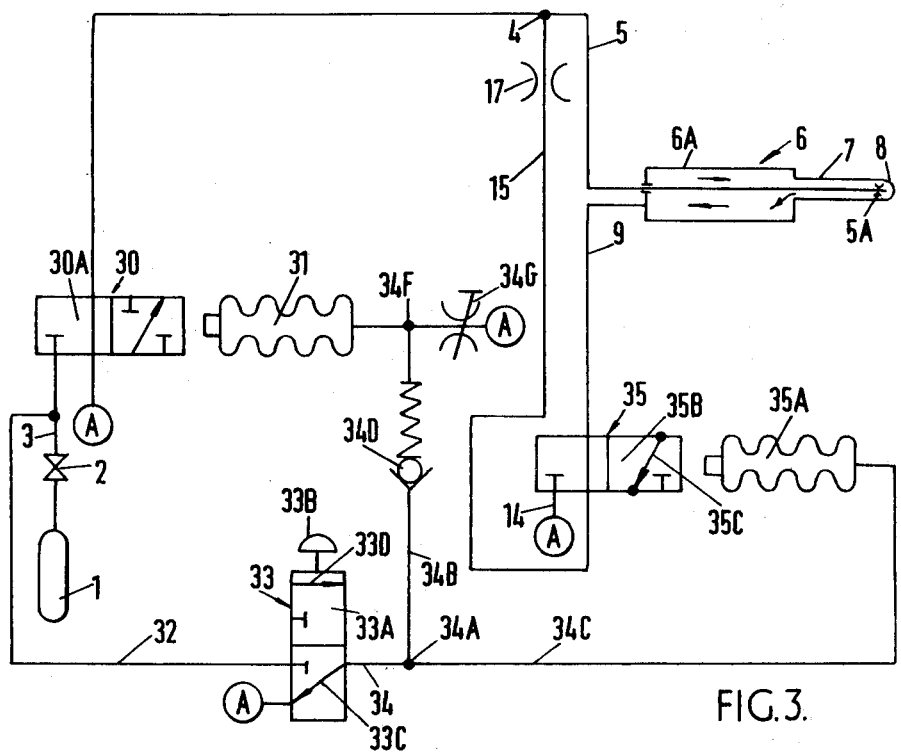
FIG. 3 is a diagram of a somewhat more elaborate system provided according to the invention, illustrated in the inoperative or "off" situation. Where it is clearer to do so, different references are shown.
Figure 4:
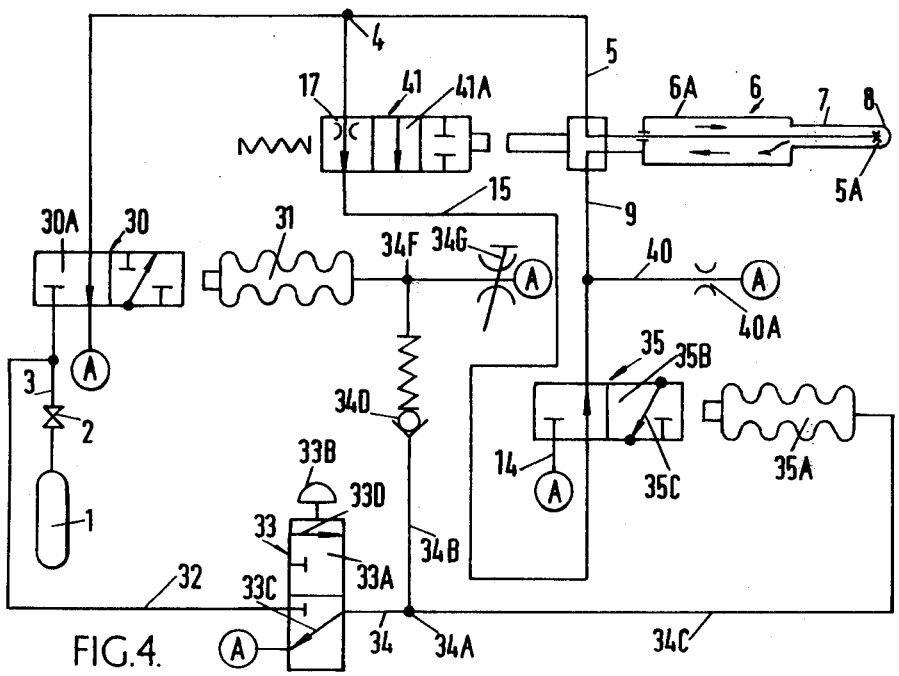

FIG. 4 is a diagram illustrating a variant of FIG. 3, in which it is provided that the operator may dictate which of three different usages he may select, the three being (i) according to the original proposal earlier mentioned and attributable to Amoils and later Wallach, namely simple exhaust-blocking for the warming mode, (ii) according to the Ritson and Thomas concept of exhaust blocking and simultaneously supplying fluid to the cavity for warming through a duct which is separate from that of the refrigerant supplied in the cooling mode, (iii) in the manner of the present invention. Again, where clarity so indicates, different references are shown.

Figure 1:
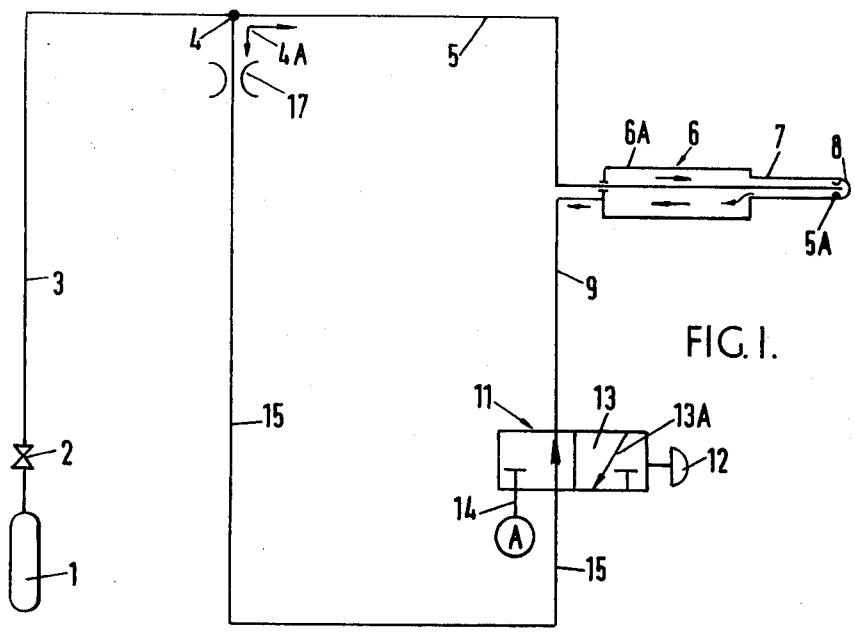
FIG. 1 illustrates an embodiment of the system which is in this Figure indicated in the warming mode.

FIG. 1 indicates a bottle 1, being a source of compressed refrigerant gas, the flow from which is generally controlled by an on-off valve 2 (which may, as is usual, be incorporated with a pressure-control valve automatically establishing constant effective pressure (later referred to as the source pressure) derived from the source 1. The gas is led via line 3 to a junction at 4 at which there is a two-way valve, the arrow 4A indicating the gas path according to the respective mode. Thence, in the cooling mode (which is the alternative to the illustrated position) gas is supplied via a first supply duct 5, which is preferably a flexible pipe of substantial length, to the hand-held instrument generally indicated at 6. The piping 3, 5, may be of such length and material as to act as a heat exchanger restoring the stream of gas threin to ambient temperature if the gas has been appreciably cooled by pressure-drop at the valve 2. In this example the instrument 6 is intended to be an Amoils-type Joule-Thomson-cooled instrument having a probe 7 with a tip 8 of high thermal conductivity enclosing the usual refrigeration cavity which receives gas through first refrigerating flow restriction means conventionally indicated at 5A from which cooled gas emerges in close proximity to and so as to impinge against the wall of the cavity of the tip 8. An example of the practical construction of such a probe is to be seen in U.S. Pat. No. 3,913,581. The cavity within the tip 8 is connected through the hollow interior of the probe 7 and its (as usual) insulated hand-held body 6A, with an exhaust duct 9 (again preferably a flexible pipe) which leads to a valve unit 11. The counterflow of gas to and from the cavity may afford some regenerative cooling of the incoming stream and the piping of ducts 5 and 9 may be coaxial for that purpose. The valve of the unit 11 is adapted for operation by manual or pedal control, or relayed means, all of which are well known in the art, indicated conventionally by the button 12 which controls the operational position of a sliding valve spool 13 within the unit 11. From the valve unit 11 there is an exhaust duct 14 leading to atmosphere (A) (usually, remotely from the site of operation for reasons of sterility because the refrigerant in its source may not be reliably sterile). The valve unit 11 is also connected by a second supply duct 15 which duct 15 is selectively connected with the first duct 5, at the junction 4. In the second duct 15 is the second restriction of the invention conventionally indicated at 17.

FIG. 1 as drawn indicates the warming mode. With the spool 13 in the drawing moved to the right, by moving the knob 12 (as drawn), connection between 9 and 14 is blocked and connection between 4, 9, 17, 15 is opened to establish the warming mode. By selectively changing the valve at 4 at a rate of flow controlled by the second restriction 17 gas flows to the valve unit 11 and thus via 9 to the probe tip 8 in opposition to the flow of gas coming through 5 and 5A. This results in the pressure within the probe (in the cavity of tip 8) gradually increasing and becoming stable and equal to the source pressure in the duct 5. This results in condensation in the cavity of the tip 8, and consequent warming of the tip. The slanted arrow 13A indicates the path in spool 13 of the valve which in the cooling mode is such that it connects 9 with 14, when spool 13 is to the left; thus the tip cavity is freely vented to atmosphere in this cooling mode.

Figure 2:
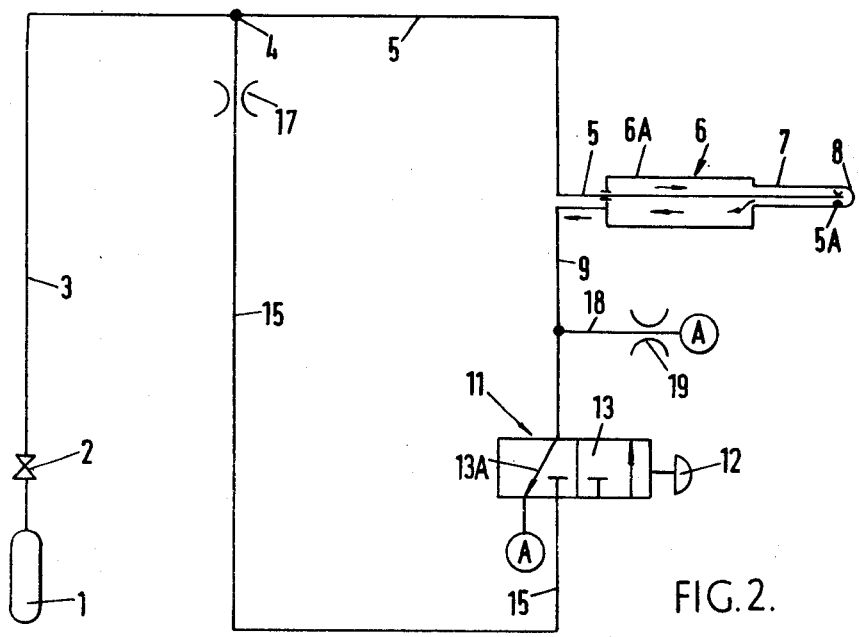
FIG. 2 is a similar diagram indicating a variant of the same system, now in the cooling mode, in which there is a restricted vent to atmosphere from the exhaust passage.

In FIG. 2 a similar system is shown and like references are shown whereby they are applicable. The diagram shows the cooling mode. In this slightly more elaborate variant there is provided a restricted bleed connection to atmosphere. It takes the form of a duct 18 branched from exhaust duct 9 to atmosphere at A. In duct 18 is a third flow restriction 19. When the valve unit 11 is operated alternatively to the way illustrated from the cooling mode drawn to the warming mode, by positioning its spool 13 to the left, so that 9 is connected to 15 (and so is 18) there is allowed, subject to the rate of flow being restricted by 19, some bleed from 9 (and therefore in effect, from the probe tip cavity) this being a gas flow to atmosphere or, as it may be termed, being a vent. Observe that in the warming mode, as above said 9 and 15 are interconnected, but direct connection between 9 and 14 is blocked. In this variant of the system, the flow to atmosphere at A via 18 may serve to purge condensate from the probe and related ducting, so that a greater heat input (i.e. warming effect) at the probe tip 8, is possible.

FIG. 3 illustrates a system according to the invention, in the "off" situation. The source 1 of pressurised gas is supplied subject to the "on-off" valve 2 and thence to the line 3. A spool valve indicated at 30 with movable spool 30A is actuated by a pressure servomotor bellows 31. As shown, the line 3 is cut off in the valve 30, but it has a branch line 32 which leads to a second spool valve 33 having a spool 33A, movable by a button (or any other control) 33B. When the spool 33A is as drawn, line 32 is cut off. If button 33B be depressed, line 32 is connected to line 34. Line 34 is branched at 34A into two lines, 34B and 34C. Line 34B leads through a check-valve 34D to a second branch at 34F respectively to the bellows 31 and through a restriction 34G to atmosphere A. The restriction 34G may be variable; for example it may be a needle-valve adapted for manual control. The branched line 34C leads to a second bellows 35A which is the actuator for a second spool valve 35 which has a spool 35B. The valve 35 has two effective positions. As illustrated, it connects the second duct 15 to the cavity of the probe in the instrument 6, and this is of course, representative of the warming mode. If the bellows 35A is effectively pressurised (through 32, 33, 34C) the spool 35B is moved to the left and consequently the probe cavity is vented via 9, 35, and 14, to atmosphere at A.

In the situation illustrated, the instrument is inoperative. Let it be assumed that the supply valve 2 is opened. The instrument is now ready for use. The cavity of the instrument, through 5 and 30, is vented freely to atmospheric pressure. The bellows 31 is vented via 34F and 34G to atmosphere. The bellows 35A, via 34C, 34 and the slanted passage 33C in spool 33A, is likewise vented to atmosphere.

The operator now requires the cooling mode. He fully depresses the button 33B. This opens 32 to 34 via passage 33D. Bellows 31 and 35A are now expanded and move spools 30A and 35B to the left. This opens 3 to 5, and 9 to 14, so that gas flows through the probe in the refrigerating (cooling) mode, the expanded gas being vented via 9 and slanted passage 35C to 14 and thus to atmosphere. In this action, 15 has been disconnected from 9 by the movement (to the left) of spool 35B. Now consider that the warming mode is required. The operator relaxes the depression of the button 33B, which rises to the position shown in FIG. 3; 34B and 34C are again opened to atmosphere via 33C, thus relieving the pressure from 35A; but because of the check valve 34D, pressure in 31 is only relieved at a slower rate, controlled by the restriction 34G.

Relaxation of bellows 35A instantly causes spool 35B to move to the right, restoring connection between 9 and 15. The probe cavity is now connected to the source 1 by two parallel paths, i.e. through the refrigerating restriction 5A in the probe and the second restriction 17. Pressure in the cavity is thus built up and condensation within it results in the required warming.

Meanwhile, relaxation of pressure in bellows 31 causes movement of spool 30A to the right but subject to restriction of flow through 34G (valve 34D being closed) so that this movement of spool 35B is retarded, and source 1 is disconnected from duct 5 (and duct 15) slowly. The rate of decay is governed by the restriction 34G which is preferably manually adjustable. The rate of warming of the probe depends partly on the pressure decay but mainly on the relative impedance of restrictions 5A and 17. When the pressure in 5, the probe tip cavity, 9, and 15 has fallen to the ambient pressure (because it is vented to atmosphere through valve 30) the whole instrument has reverted to the original "off" condition, and the surgeon can start another cycle of cooling and warming merely by using the button 33B.

FIG. 4 uses a system similar to that of FIG. 3, but varied in two respect. Where they are repeatable, the references are the same as in FIG. 3. In addition, there is a further vent to atmosphere A, via a branch exhaust line 40 which has a restriction at 40A. 40 is branched from the duct 9 and permanently vents the tip cavity and duct 9. Be it noted, however, that when the valve is in the cooling mode, 9 is freely open to atmosphere (through passage 35C). Thus only in the warming mode (as illustrated) is restriction 40A appreciably effective. Its presence provides that, in the warming mode there is vented flow of fluid from the probe and associated passages, and this may serve to purge condensate with the advantage previously stated, of enhancing the desired warming.

Also to be seen in FIG. 4 is a further valve, indicated at 41 with a spool 41A. This valve is interposed in the duct 15. It has three possible positions and is intended either for manual operation or, as is preferred, by the way in which a pipe-connector is connected. In the position shown, duct 15 is connected to 4 (and therefore to duct 5) through the second restriction 17 and the situation is the same as that of FIG. 3. If the spool 41A is moved to the left through about half its available travel, unimpeded connection is made between 4 and 15; this may be described as the "Ritson and Thomas" situation, the source 1 being unrestrictedly connected to the probe tip in the warming mode. If the spool 41A is moved fully to the left, 4 is wholly cut off from 15 and the situation is that of the Amoils-Wallach device, in which the exhaust or venting from the tip cavity is blocked.

In embodiments such as that shown in FIGS. 3 and 4, in the warming or "decay" phase, refrigerant present in the probe is, as above stated, vented to atmosphere at a rate which is relatively slow by reason of the flow restriction 34G to such venting, so that during this phase evaporation of condensed refrigerant within the cavity and/or adjacent passages is retarded, with the object of reducing tendency of the probe applicator to re-cool at the end of the pressure decay cycle, which tendency may occur when practising the previously referred to invention described in U.S. Pat. No. 3,913,581, i.e. the Ritson and Thomas invention.

The foregoing description shows examples in which there are always two ducts from source to cavity, the flow in each (when in appropriate mode) being controlled by the respective restriction. However, in the warming mode, the flow in the second duct may (as in the Ritson and Thomas proposal) be unresisted by a restriction between source and cavity but instead, be resisted by a vent restriction in a vent to atmosphere through which vent, in the warming mode, the warming fluid escapes subject to the resistance caused by the vent restriction. In such a case the vent restriction is the second restriction and it controls the flow into the cavity. Looking at FIG. 2, for example, it can therefore be understood that the restriction 17 may be omitted, and warming mode control be provided by restriction 19.

Previous mention has been made of adaptability. This has special reference to the manner in which the second restriction (17) is provided. Whilst the range of operation of this restriction may be considerably wider than of the first (5a) it may nevertheless be desirable to provide in a console or even a self-contained hand-held instrument, a second restriction 17 which is designed for easy replacement by another of different characteristics. Or, to provide two or more restrictions which can be brought into simultaneous use in parallel, so as to have the same effect as a single larger one.

Moreover, the on/off valve above referred to (e.g. 2 in FIGS. 1 and 2, or 32 in FIG. 3) may be designed in known manner so that it is operated by the connection or disconnection of the supply line (e.g. 3) to the source, or likewise the connection of the ducting to a console. Thus, for example, a plug-in type of connector may be used, and by simple adaptation be such as to operate a control e.g. the so-called foot switch, so that the instrument is made ready for use simply by "plugging in". Thus, the removable part of a connector may be formed with an abutment to contact and push a button (e.g. 12) or an equivalent control device when connection is made.

We claim:

1. In a cryogenic instrument of the type having selective cooling and warming modes of operation and in which fluid from a pressurized source is fed to a cavity of a probe through a first duct and through first restriction means in the probe to produce a pressure-drop resulting in the required cooling of a wall of the cavity during the cooling mode, a second duct for connecting a source of pressurized fluid to said cavity separately from said first duct and said first restriction means during the warming mode, said second duct having associated therewith second restriction means for controlling the flow of fluid through said second duct during the warming mode, and valve means for selectively connecting said first duct to said cavity during the cooling mode to produce said pressure drop and for connecting both said ducts to the cavity during the warming mode to pressurize the cavity and produce condensation therein, the flow impedance of the first and second restriction means being so related as to control the relative flows of fluid into the cavity via said ducts during the warming mode.

2. An instrument in accordance with claim 1, wherein said pressurized source from which fluid is fed to the cavity during the cooling mode is a source of polyatomic gas and wherein cooling is produced by the Joule-Thomson effect.

3. An instrument in accordance with claim 2, wherein the pressurized source from which fluid is fed to the cavity through the first duct during the cooling mode is the same as the source of pressurized fluid connected to the cavity by the second duct during the warming mode.

4. An instrument in accordance with claim 1, wherein the second restriction means is in the second duct.

5. An instrument in accordance with claim 1, wherein the second restriction means is in a bleed to the atmosphere from said second duct.

6. An instrument in accordance with claim 1, wherein said valve means connects said cavity to the atmosphere through a portion of said second duct during the cooling mode.

7. An instrument in accordance with claim 1, wherein said second restriction means is remote from said probe.

8. An instrument in accordance with claim 1, further comprising means for purging said cavity of liquid.

9. An instrument in accordance with claim 1, further comprising means for bleeding the pressurized fluid in said cavity to the atmosphere during the warming mode.

10. An instrument in accordance with claim 9, wherein the last-mentioned means comprises a third duct having third restriction means.

11. An instrument in accordance with claim 1, wherein the instrument includes means for permitting the operator of the instrument to select the flow impedance of the second restriction means.

12. An instrument in accordance with claim 1, further comprising valve means for selectively providing flow through said second duct unrestricted by said second restriction means during the warming mode.

13. An instrument in accordance with claim 1, further comprising valve means for selectively pressurizing said cavity during the warming mode through said first duct only.

14. An instrument in accordance with claim 1, further comprising valve means for selectively providing three types of operation during said warming mode: one type in which the flow through said second duct is controlled by said second restriction means, a second type in which the flow through said second duct is not controlled by said second restriction means, and a third type in which said second duct is blocked and said cavity is pressurized through said first duct.

15. An instrument in accordance with claim 1, wherein said valve means comprises a fluid-actuated valve controlled by the operator of the instrument.

16. An instrument in accordance with claim 1, wherein said valve means comprises a pair of fluid-actuated valves controlled by the operator of the instrument, one of said fluid-actuated valves being effective to place the instrument in the cooling mode or the warming mode selectively and the other of the fluid-actuated valves being effective to connect the cavity to the atmosphere after the instrument has been placed in the warming mode.

17. An instrument in accordance with claim 16, wherein said other valve also connects said first and second ducts to the atmosphere after the instrument has been placed in the warming mode.

18. An instrument in accordance with claim 16, wherein said other valve automatically connects said cavity to the atmosphere at a time delayed relative to the beginning of the warming mode.

19. An instrument in accordance with claim 1, wherein said cavity is permanently vented to the atmosphere through a restriction.

* * * * *